*US012102354B2*

United States Patent
Hristov et al.

(10) Patent No.: US 12,102,354 B2
(45) Date of Patent: Oct. 1, 2024

(54) IMPLANT DELIVERY SLEEVES HAVING NON-TAPERED TUBULAR WALLS WITH CONSTRICTED IMPLANT DELIVERY CHANNELS FOR INSERTING IMPLANTS INTO TISSUE POCKETS

(71) Applicant: Mentor Worldwide LLC, Irvine, CA (US)

(72) Inventors: Krasimira Hristov, Hillsborough, NJ (US); Leo B. Kriksunov, Ithaca, NY (US); Robert J. Tannhauser, Bridgewater, NJ (US); Marc Feinberg, Ringoes, NJ (US)

(73) Assignee: Mentor Worldwide LLC, Irvine, CA (US)

( * ) Notice: Subject to any disclaimer, the term of this patent is extended or adjusted under 35 U.S.C. 154(b) by 577 days.

(21) Appl. No.: 17/489,087

(22) Filed: Sep. 29, 2021

(65) Prior Publication Data

US 2023/0098318 A1    Mar. 30, 2023

(51) Int. Cl.
*A61B 17/34* (2006.01)
*A61B 17/00* (2006.01)

(52) U.S. Cl.
CPC .............. *A61B 17/3468* (2013.01); *A61B 2017/00792* (2013.01); *A61B 2017/00796* (2013.01); *A61B 2017/00862* (2013.01)

(58) Field of Classification Search
CPC ...... A61B 17/3468; A61B 2017/00792; A61B 2017/00796; A61B 2017/00862; A61F 2/12
See application file for complete search history.

(56) References Cited

U.S. PATENT DOCUMENTS

| 4,035,850 A | 7/1977 | Cresswall |
| 4,955,906 A | 9/1990 | Coggins et al. |

(Continued)

FOREIGN PATENT DOCUMENTS

| CA | 2760551 | 11/2010 |
| CA | 2861438 | 8/2013 |

(Continued)

OTHER PUBLICATIONS

Mladick, Richard A., "No-Touch Submuscular Saline Breast Augmentation Technique," Aesthetic Plastic Surgery, 1993, pp. 183-192, vol. 17.

(Continued)

*Primary Examiner* — Sarah W Aleman
*Assistant Examiner* — Rachel S Highland
(74) *Attorney, Agent, or Firm* — Troutman Pepper Hamilton Sanders LLP

(57) ABSTRACT

An implant delivery sleeve comprises a tubular wall having a proximal end with a proximal opening, a distal end with a distal opening, and an implant delivery channel extending between the proximal and distal ends of said tubular wall. A plurality of bands interconnect portions of the tubular wall for constricting the implant delivery channel adjacent the distal end of the tubular wall. As an implant is advanced toward the distal end of the tubular wall, the constriction squeezes and/or deforms the implant for facilitating insertion into an incision that is smaller than the normal size of the implant.

18 Claims, 7 Drawing Sheets

(56) References Cited

U.S. PATENT DOCUMENTS

| | | | |
|---|---|---|---|
| 5,201,779 A | 4/1993 | Shiao | |
| 5,723,006 A | 3/1998 | Ledergerber | |
| 7,137,995 B2 | 11/2006 | Studin | |
| 7,935,089 B2 | 5/2011 | Tsao | |
| 8,206,443 B2 | 6/2012 | Preissman | |
| 8,211,173 B2 | 7/2012 | Keller et al. | |
| 8,409,279 B2 | 4/2013 | Freund | |
| 8,550,090 B2 | 10/2013 | Keller et al. | |
| 8,555,893 B2 | 10/2013 | Keller et al. | |
| 8,641,758 B1 | 2/2014 | Anderson et al. | |
| D736,372 S | 8/2015 | Anderson | |
| D738,490 S | 9/2015 | Anderson | |
| 9,168,126 B2 | 10/2015 | Preissman | |
| D752,739 S | 3/2016 | Anderson | |
| 9,399,122 B2 | 7/2016 | Mosharrafa et al. | |
| 9,402,713 B2 | 8/2016 | Keller et al. | |
| 9,414,941 B2 | 8/2016 | Placik et al. | |
| 9,474,593 B2 | 10/2016 | Anderson | |
| D773,652 S | 12/2016 | Anderson | |
| D775,725 S | 1/2017 | Anderson | |
| D776,806 S | 1/2017 | Anderson | |
| 9,615,908 B2 | 4/2017 | Anderson | |
| 9,730,728 B2 | 8/2017 | Anderson | |
| 9,782,251 B2 | 10/2017 | Anderson | |
| 9,808,284 B2 | 11/2017 | Anderson | |
| 9,808,285 B2 | 11/2017 | Anderson | |
| 9,925,028 B1 | 3/2018 | Rosenberg | |
| 9,936,973 B2 | 4/2018 | Anderson et al. | |
| 10,058,415 B2 | 8/2018 | Preissman | |
| 10,092,385 B2 | 10/2018 | Anderson | |
| 10,105,213 B2 | 10/2018 | Weinzweig | |
| 10,136,988 B2 | 11/2018 | Keller et al. | |
| 10,213,294 B2 | 2/2019 | Keller et al. | |
| 10,575,936 B2 | 3/2020 | Rosenberg | |
| 2007/0038310 A1 | 2/2007 | Guetty | |
| 2007/0276484 A1 | 11/2007 | Abell et al. | |
| 2009/0204107 A1 | 8/2009 | Keller et al. | |
| 2011/0082546 A1* | 4/2011 | Freund | A61F 2/12 623/8 |
| 2014/0228951 A1 | 8/2014 | Zochowski | |
| 2015/0032208 A1 | 1/2015 | Preissman | |
| 2016/0038275 A1 | 2/2016 | Preissman | |
| 2016/0199174 A1 | 7/2016 | Keller et al. | |
| 2017/0100233 A1 | 4/2017 | Zochowski | |
| 2017/0181841 A1 | 6/2017 | Weinzweig | |
| 2018/0070984 A1 | 3/2018 | Anderson | |
| 2018/0116779 A1 | 5/2018 | Marx | |
| 2018/0325654 A1 | 11/2018 | Preissman | |
| 2018/0368963 A1 | 12/2018 | Anderson | |
| 2019/0117365 A1 | 4/2019 | Winn | |
| 2019/0274817 A1 | 9/2019 | Hristov et al. | |
| 2019/0274818 A1 | 9/2019 | Hristov et al. | |
| 2019/0274819 A1 | 9/2019 | Graf et al. | |
| 2019/0328506 A1 | 10/2019 | Keller et al. | |
| 2020/0008923 A1* | 1/2020 | Geiger | A61B 17/3431 |

FOREIGN PATENT DOCUMENTS

| | | |
|---|---|---|
| CN | 201076483 Y | 6/2008 |
| CN | 208492395 U | 2/2019 |
| CN | 208611049 | 3/2019 |
| CN | 209827102 U | 12/2019 |
| EP | 2723414 | 4/2017 |
| WO | 2012177587 | 12/2012 |
| WO | 2019014075 | 1/2019 |

OTHER PUBLICATIONS

Mladick, Richard A., "Finesse in Breast Augmentation Through Use of the 'No-Touch' Technique," Aesthetic Surgery Journal, Nov./Dec. 1999, pp. 489-497, vol. 19, No. 6.

* cited by examiner

IMPLANT DELIVERY SLEEVES HAVING NON-TAPERED TUBULAR WALLS WITH CONSTRICTED IMPLANT DELIVERY CHANNELS FOR INSERTING IMPLANTS INTO TISSUE POCKETS

BACKGROUND OF THE INVENTION

Field of the Invention

The present patent application is generally related to medical devices and procedures, and is more particularly related to systems, devices, and methods for inserting implants into tissue pockets.

Description of the Related Art

Tapered flexible sleeves, such as those marketed under the brand name KELLER FUNNEL®, may be used as a delivery device for implanting a silicone-gel breast implant into a patient. The KELLER FUNNEL® sleeves permit delivery of the implant through an incision that is shorter than it would need to be if the sleeve were not used. Using implant delivery sleeves may also lower the likelihood of introducing contaminants, e.g., microorganisms, into the patient through the incision because they minimize the amount of contact between the implant, the surgeon's hands, and the patient's tissue.

A number of U.S. patents have been issued on the technology incorporated into the KELLER FUNNEL® sleeves, including U.S. Pat. No. 8,211,173 to Keller et al., which discloses a delivery system for inserting a silicone breast implant into a surgical pocket. The system includes a silicone implant, and a tapered, flexible sleeve having an interior extending between a first opening and a second opening. The first opening is sized to receive the silicone implant and is relatively larger than the second opening. The silicone implant is in lubricious contact with the interior of the sleeve and the sleeve is manually manipulated to slide the silicone implant along the interior and through the second opening.

U.S. Pat. No. 8,555,893 to Keller et al. discloses a method of using a tapered sleeve to insert a silicone breast implant located within the sleeve into a surgical pocket in a breast of a human patient. The sleeve has a first opening and a second opening, whereby the first opening is relatively larger than the second opening. The method includes closing the first opening, grasping the silicone breast implant through the sleeve, and applying manual pressure through the sleeve to the silicone breast implant to push the silicone breast implant toward and through the second opening, without direct hand manipulation of the silicone breast implant, until the silicone breast implant is deposited from the second opening into the surgical pocket.

In addition to the Keller patents, there have been many other technological advances directed to providing sleeves for delivering implants into surgical pockets. For example, US 2019/0274817 to Hristov et al., assigned to Mentor Worldwide LLC, the disclosure of which is hereby incorporated by reference herein, teaches an implant delivery sleeve including an enclosure having at least one opening and at least one vent conduit. The vent conduit extends along a surface of the enclosure to assist in removing fluids (e.g., air) from the tissue pocket to facilitate implantation of the implant into a patient.

US 2019/0274818 to Hristov et al., assigned to Mentor Worldwide LLC, the disclosure of which is hereby incorporated by reference herein, teaches an implant delivery sleeve including a tube having three segments. The first segment has a first stiffness, the second segment has a second stiffness, and the third segment has a third stiffness. The third stiffness is greater than the second stiffness and the second stiffness is greater than the first stiffness. The implant delivery sleeve is used to deliver a breast implant to a subject. The implant may be deformed within the sleeve, to advance it within the sleeve and extrude it from the distal end of the sleeve.

US 2019/0274819 to Graf et al., assigned to Mentor Worldwide LLC, the disclosure of which is hereby incorporated by reference herein, teaches an implant delivery sleeve for assisting in the delivery of a tissue implant. The delivery sleeve has an enclosure, an orifice, and a throat. A cinching mechanism (e.g., a fastener) is disposed about the throat. The fastener may be used to fasten the cinching mechanism in a cinched configuration to maintain the throat in a closed configuration. The cinching mechanism may include implant-size indicators provided thereon. A lubricant or lubricious material may be included upon an inner surface of the enclosure. The cinching mechanism is used to change the configuration of the throat from an open configuration to a closed configuration. The fastener helps to maintain the throat in a closed configuration.

In spite of the above advances, there is a continuing need for improved implant delivery sleeves that facilitate delivering implants into tissue pockets.

The is also a need for improved implant delivery sleeves that are capable of squeezing implants (e.g., breast implants filled with silicone gel) through constrictions that are substantially smaller than the normal size of the implant so that the implant can be inserted into an incision opening that is smaller than the normal size of the implant.

SUMMARY OF THE INVENTION

In one embodiment, implant delivery sleeves may be utilized for delivering implants (e.g., breast implants) into incisions or tissue pockets.

In one embodiment, the implant delivery sleeves may be non-tapered, non-frustoconical, and/or non-funnel shaped.

In one embodiment, an implant delivery sleeve may include a tubular wall (also referred to as a tube-shaped wall) having a generally elongated, hollow, cylindrical shape.

In one embodiment, the tube-shaped wall may have a non-tapered shape and may have proximal and distal end openings that are the same size.

In one embodiment, bands (e.g., rivets; mechanical links) preferably interconnect distal portions of the tubular wall for constricting the passage of objects through an implant delivery channel of the implant delivery sleeve.

In one embodiment, the bands may be in one plane or in several planes.

In one embodiment, one or more bands may have a rotatable mid-section for facilitating movement of implants through an implant delivery channel of an implant delivery sleeve.

In one embodiment, the bands are located closer to the distal end of the tubular wall than the proximal end of the tubular wall.

In one embodiment, bands that are closer to the distal end of the tubular wall are closer to the middle axis of the tubular wall.

In one embodiment, the bands that are farther from the distal end of the tubular wall are also farther from the middle axis of the tubular wall.

In one embodiment, the height of the bands decreases as the bands are closer to the distal end of the tubular wall and closer to the middle axis of the tubular wall.

In one embodiment, the height of the bands increases as the bands are farther from the distal end of the tubular wall and farther from the middle axis of the tubular wall.

In one embodiment, the bands are all installed at the same distance from the middle axis, however, the respective heights of the bands decrease as the bands are located closer to the distal end of the tubular wall.

In one embodiment, pairs of bands are installed equidistantly from the middle axis, opposite each other at certain distances from the middle axis.

In one embodiment, an implant delivery sleeve may have three sets of bands, four sets of bands, or more than four sets of bands installed equidistantly from the middle axis of the tubular wall, at a predetermined distance from the middle axis In one embodiment, an implant delivery sleeve preferably includes a tube-shaped wall (also referred to as a tubular wall) having a proximal end with a proximal opening, a distal end with a distal opening, and an implant delivery channel extending between the proximal and distal openings of the tube-shaped wall.

In one embodiment, a plurality of bands (e.g., rivets) interconnect portions of the tube-shaped wall for constricting the implant delivery channel adjacent the distal end of the tube-shaped wall.

In one embodiment, at least some of the bands define a constricted opening in the tube-shaped wall that is located adjacent and/or at the distal end of the tube-shaped wall.

In on e embodiment, the proximal and distal openings of the tube-shaped wall have the same size.

In one embodiment, the constricted opening formed by the bands has a smaller size (e.g., has a smaller width, height and/or area) than the size of the distal opening at the distal end of the tube-shaped wall.

In one embodiment, the tube-shaped wall of the implant delivery sleeve may comprise an elastomeric material.

In one embodiment, at least some of the bands that form the constriction lie in a single plane.

In one embodiment, at least some of the bands that form the constriction lie in different planes.

In one embodiment, at least some of the bands are configured for engaging an implant (e.g., a silicone breast implant) as the implant passes through the implant delivery channel for squeezing, deforming and/or constricting the implant within the implant delivery channel.

In one embodiment, at least one of the bands preferably comprises a rotatable middle section that is configured for engaging the implant to facilitate movement of the implant through the implant delivery channel of the tube-shaped wall of the implant delivery sleeve.

In one embodiment, the tubular wall of the implant delivery sleeve desirably has a middle axis that extends from the proximal end to the distal end of the tubular wall.

In one embodiment, the middle axis extends along the length of the tube-shaped wall and may define the longitudinal axis of the tube-shaped wall.

In one embodiment, the bands that form the constriction preferably have respective heights that decrease as the bands are closer to the distal end of the tube-shaped wall.

In one embodiment, the bands that form the constriction preferably have respective heights that decrease as the bands are closer to the middle axis of the tube-shaped wall.

In one embodiment, the bands that form the constriction are preferably equidistant from the middle axis of the tube-shaped wall and have respective heights that decrease as the bands are closer to the distal end of the tube-shaped wall.

In one embodiment, the bands may include pairs of bands that are equidistant from the middle axis of the tube-shaped wall of the implant delivery sleeve. The respective pairs of bands are desirably located on opposite sides of the middle axis.

In one embodiment, at least some of the bands that form the constriction in the tube-shaped wall of the implant delivery sleeve are elastic.

In one embodiment, the bands closer to the distal end of the tube-shaped wall may be more elastic than the bands that are farther away from the distal end of the tube-shaped wall.

In one embodiment, the bands that form the constriction may include a first set of the bands that are more elastic and a second set of the bands that are less elastic than the first set of the bands.

In one embodiment, an implant delivery sleeve is adapted to delivery an implant (e.g., a breast implant filled with a silicone gel) into an incision or a tissue pocket of a patient.

In one embodiment, the implant delivery sleeve preferably includes a tube-shaped outer wall having a proximal end with a proximal opening, a distal end with a distal opening, and an implant delivery channel extending from the proximal opening to the distal opening of the tube-shaped outer wall.

In one embodiment, a plurality of bands are disposed inside the tube-shaped outer wall and interconnect opposing sections of the tube-shaped outer wall for constricting the implant delivery channel that extends along the length of the tube-shaped outer wall. In one embodiment, the bands constrict the implant delivery channel adjacent the distal end of the tube-shaped outer wall.

In one embodiment, at least some of the bands define a constricted opening that is located adjacent or at the distal end of the tube-shaped outer wall.

In one embodiment, the bands have respective heights that decrease as the bands are closer to the distal end of the tube-shaped outer wall.

In one embodiment, the bands have respective heights that decrease as the bands are closer to the middle axis of the tube-shaped outer wall.

In one embodiment, a method of using an implant delivery sleeve preferably includes obtaining a tube-shaped wall having a proximal end with a proximal opening, a distal end with a distal opening, and an implant delivery channel extending between the proximal and distal openings of the tube-shaped wall, the flexible sleeve including a plurality of bands interconnecting portions of the tube-shaped wall for constricting the size of the implant delivery channel adjacent the distal end of the tube-shaped wall.

In one embodiment, a method of using an implant delivery sleeve preferably includes inserting an implant (e.g., a breast implant) into the proximal opening of the tube-shaped wall of the implant delivery sleeve so that a distal end of the silicone breast implant is disposed within the implant delivery channel.

In one embodiment, a method of using an implant delivery sleeve preferably includes engaging an outer surface of the tube-shaped wall for closing the first opening at the proximal end of the tube-shaped wall to encapsulate the implant within the tube-shaped wall of the implant delivery sleeve.

In one embodiment, a method of using an implant delivery sleeve preferably includes squeezing the tube-shaped wall for applying manual pressure to the implant to push the implant toward the distal end of the implant delivery channel for extruding the implant from the distal end of the tube-shaped wall of the implant delivery sleeve.

In one embodiment, a method of using an implant delivery sleeve preferably includes forming an incision in a patient, inserting the distal end of the tube-shaped wall into the incision, and during the extruding the implant step, passing the implant through the incision and into a tissue pocket.

These and other preferred embodiments of the present patent application will be described in more detail herein.

DETAILED DESCRIPTION OF PREFERRED EMBODIMENTS

Figure 1:
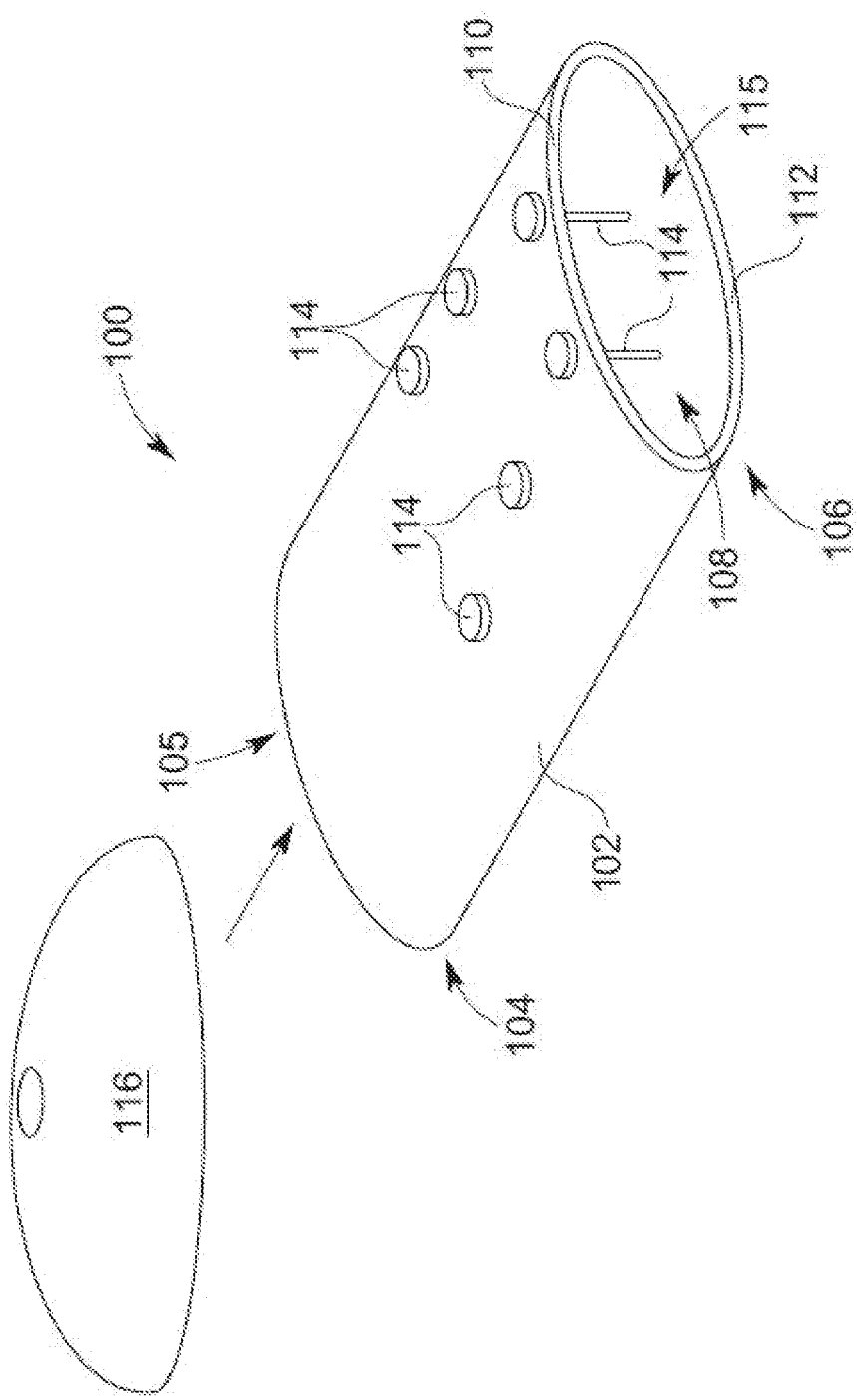
FIG. 1 is a perspective view of an implant delivery sleeve including a tubular wall that surrounds an implant delivery channel, the implant delivery sleeve including bands interconnecting portions of the tubular wall for constricting the implant delivery channel, in accordance with one embodiment of the present patent application.

Referring to FIG. 1, in one embodiment, an implant delivery sleeve 100 preferably includes a cylindrical or tube-shaped wall 102. In one embodiment, the tube-shaped wall 102 is desirably non-tapered, non-frustoconical, and/or non-funnel shaped. In one embodiment, the tube-shaped wall 102 of the implant delivery sleeve 100 preferably has a proximal end 104 that defines a proximal opening 105 (FIG. 2A) and a distal end 106 that preferably defines a distal opening 108. In one embodiment, the tube-shaped wall 102 desirably includes a first wall section 110 and an opposing second wall section 112 that are interconnected by bands 114 (e.g., mechanical fasteners; rivets) that interconnect the opposing wall sections 110, 112 to form a constriction within the implant delivery sleeve.

As used herein, the terms tube-shaped wall and tubular wall may be used interchangeably.

In one embodiment, the proximal opening 105 and the distal opening 108 of the tube-shaped wall have the same size and/or cross-sectional area.

In one embodiment, the bands 114 are configured for constricting an implant delivery channel 115 that is used for passing objects (e.g., a breast implant having a silicone gel filling) through the tube-shaped wall 102 of the implant delivery sleeve 100. In one embodiment, the bands 114 may be arranged in one plane or in several planes for directing the movement of an implant 116 along the length of the implant delivery channel 115 of the implant delivery sleeve 100.

In one embodiment, the bands 114 may constrict and/or deform the shape of the implant as it passes through the implant delivery channel. In one embodiment, the constriction and/or deformation of the implant preferably makes a portion of the implant smaller for facilitating insertion of the implant into an incision and/or tissue pocket formed in a patient.

Figure 2A:
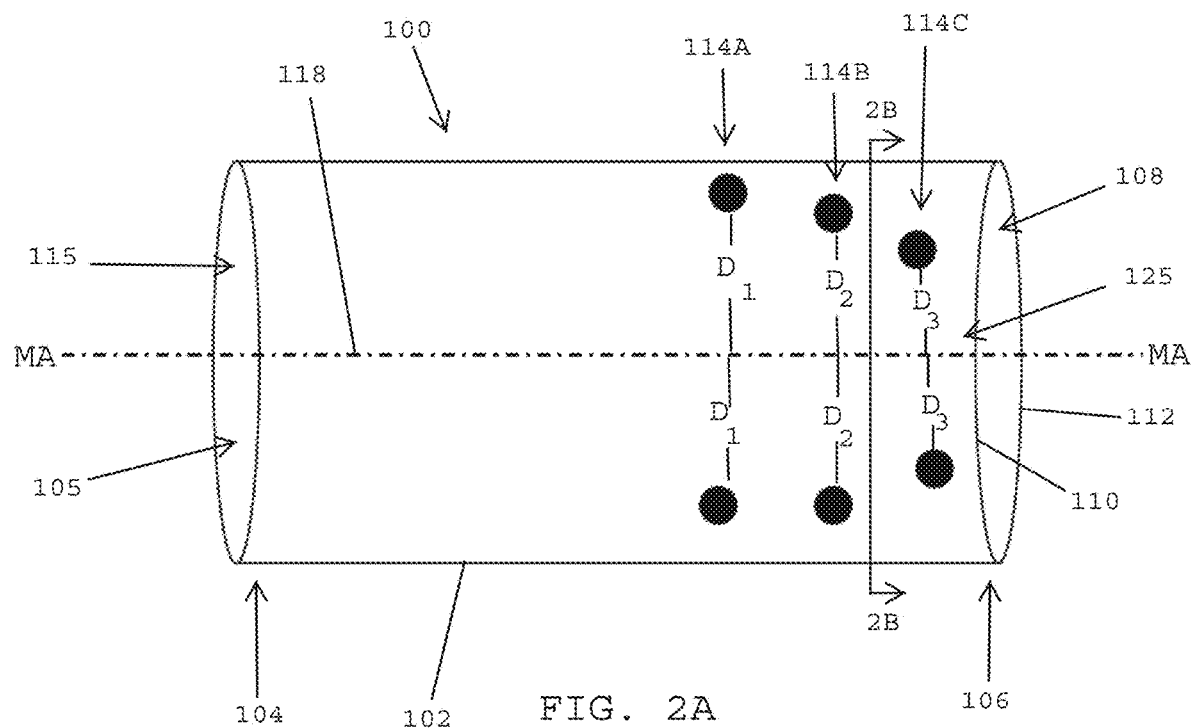
FIG. 2A is a top view of the implant delivery sleeve shown in FIG. 1.

Referring to FIG. 2A, in one embodiment, the implant delivery sleeve 100 preferably includes the tube-shaped wall 102 having the proximal end 104 that defines the proximal opening 105 and the distal end 106 that defines the distal opening 108. The implant delivery channel 115 preferably extends along the length of the tube-shaped wall 102 between the proximal opening 105 and the distal opening 108. The bands 114 (FIG. 1) preferably attach the first wall section 110 with the opposing second wall section 112 to create a constriction within the implant delivery channel 115, which is located between the proximal end 104 and the distal end 106 of the tube-shaped wall 102.

In one embodiment, the tube-shaped wall 102 of the implant delivery sleeve 100 preferably has a length that extends along a middle axis MA, which defines a midline 118 of the tube-shaped wall 102. In one embodiment, the middle axis MA extends along the longitudinal axis of the tube-shaped wall 102.

In one embodiment, the bands 114 are preferably installed closer to the distal end 106 of the tube-shaped wall 102 than the proximal end 104 of the tube-shaped wall. In one embodiment, the bands 114 (e.g., bands 114C) that are closest to the distal end 106 of the tube-shaped wall are closer to the middle axis MA of the flexible sleeve 100, and the bands (e.g., bands 114A) that are farther from the distal end 106 of the tube-shaped wall 102 are farther from the middle axis MA of the flexible sleeve 100. For example, in the embodiment shown in FIG. 2A, a proximal set of bands 114A are spaced away from the midline axis MA by a first distance $D_1$ and an intermediate set of bands 114B are spaced away from the middle axis MA by a second distance $D_2$ that is less than the first distance $D_1$. In a similar manner, a distal-most set of bands 114C is spaced away from the middle axis MA by a third distance $D_3$ that is less than the second distance $D_2$ of the intermediate bands 114B.

In one embodiment, the locations of the bands 114A-114C generally taper inwardly toward one another as the bands are located closer to the distal end 106 of the tube-shaped wall 102, thereby narrowing and/or constricting the implant delivery channel 115 adjacent the distal end 106 of the tube-shaped wall 102.

In one embodiment, the series of bands 114A-114C define a narrowing implant delivery channel that terminates with a constricted opening 125 that is located adjacent and/or at the distal end 106 of the tube-shaped wall 102. In one embodiment, the constricted opening 125 that is defined by the bands 114A-114C is smaller than the distal opening 108 at the distal end of the tube-shaped wall 102 of the implant delivery sleeve 100.

In one embodiment, an implant (e.g., a silicone gel filled breast implant) may be passed through the implant delivery sleeve 100 for being delivered from the constricted opening 125 at the distal end 106 of the tube-shaped wall 102 to be implanted into a patient, such as through an incision or into a tissue pocket formed in a patient.

Figure 2B:
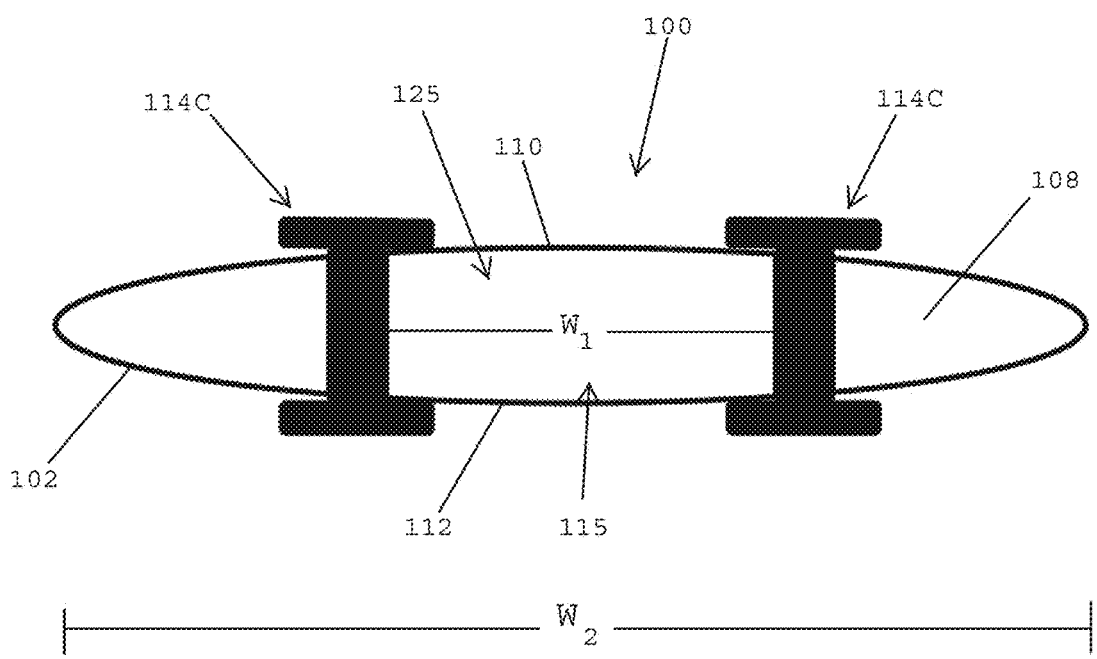
FIG. 2B is a cross-sectional view of the implant delivery sleeve shown in FIG. 2A taken along line 2B-2B of FIG. 2A.

Referring to FIG. 2B, in one embodiment, the bands 114A-114C (FIG. 2A) preferably interconnected the opposing first and second wall sections 110, 112 of the tube-shaped wall 102. The distal-most bands 114C preferably define the size of the constricted opening 125 adjacent the distal end of the tube-shaped wall 102, whereby the constricted opening 125 has a first width $W_1$ that is less than the second width $W_2$ of the distal opening 108 of the tube-shaped wall 102. In one embodiment, an implant is preferably passed between the distal-most bands 114C that define the lateral boundaries of the constricted opening 125. The implant may be constricted and/or deformed as it passes through the constricted opening 125 of the tube-shaped wall 102 of the implant delivery sleeve 100.

The implant delivery sleeve 100 may be used to deliver an implant, such as a breast implant, into a subject, such as a human patient. Breast implants typically have a diameter ranging from between approximately three inches and seven inches. Implants are typically referred to by their diameter, e.g., "a five-inch implant," and such diameters correspond to a diameter of the widest cross-section of the implant that is parallel to the base of the implant Silicone-gel implants are flexible and pliable, and may be squeezed considerably to constrain the implant in a configuration such that the diameter of the implant may be constricted considerably, e.g., on the order of between approximately 2 times and 10 times. For example, if the implant is a "three-inch implant" the portion that is three inches may be squeezed to constrict that portion to having a width of approximately 1.5 inches. Once the constrictive forces are removed, the portion recovers its original shape having a three-inch diameter. Due to the flexible nature of silicone-gel implants, an implant may be squeezed through constrictions (e.g., through the constricted opening 125 shown in FIG. 2A) that are substantially smaller than the normal size of the implant. Accordingly, the constrictions may define a passageway having an inner diameter that is between one-half (½) to one-fifth (⅕) of the implant's normal size. For example, the width $W_1$ (FIG. 2B) and/or the inner diameter of the constricted opening 125 at the distal end of the implant delivery channel 115 may be approximately 1.5 inches.

In one embodiment, the tube-shaped wall 102 of the implant delivery sleeve 100 is preferably fabricated from a material that may be elastically or plastically deformed, e.g., an elastomer such as silicone rubber, such that when an implant is passed through the tube-shaped wall 102, an outer diameter and/or an inner diameter of the tubular wall may be enlarged or dilated. Thus, the tube-shaped wall 102 may conform to the shape of an implant being passed therethrough, and the implant itself may be in a state of deformation caused by the tube-shaped wall.

Figure 3:
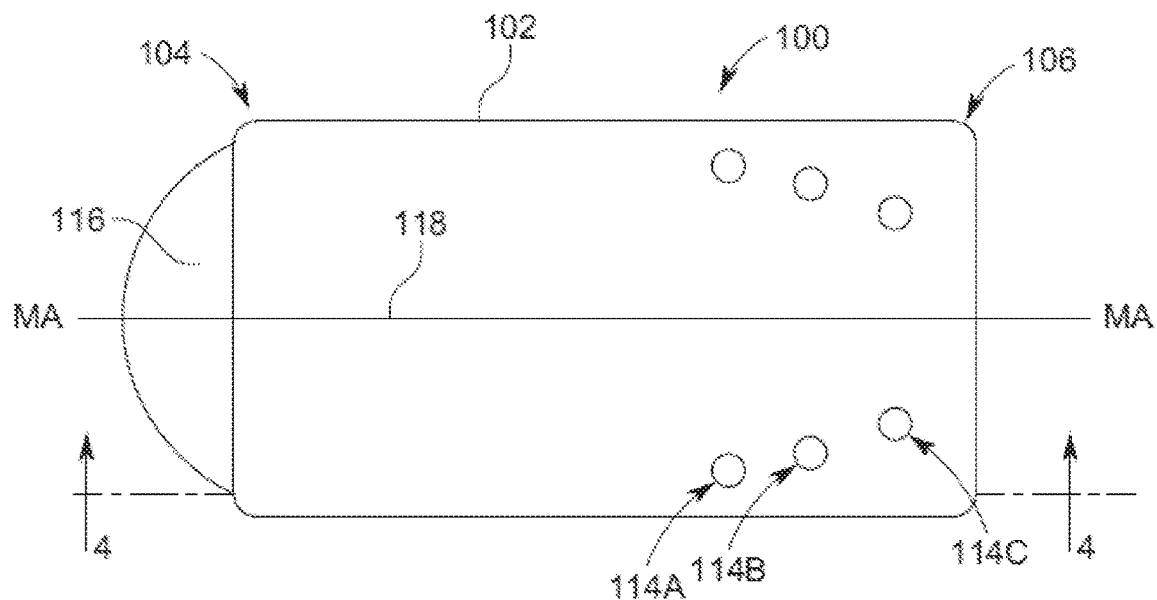
FIG. 3 is a top view of the implant delivery sleeve of FIG. 1 with an implant inserted into a proximal opening at a proximal end of the tubular wall, in accordance with one embodiment of the present patent application.

Referring to FIG. 3, in one embodiment, the implant delivery sleeve 100 preferably includes the tube-shaped wall 102 having the proximal end 104 and the distal end 106. The implant delivery sleeve 100 preferably has a length that extends along the middle axis MA that defines the midline 118 of the tube-shaped wall 102.

As described above, the series of bands 114A-114C mechanically interconnect opposing portions and/or wall sections of the tube-shaped wall 102 of the implant delivery sleeve 100. A proximal-most set of bands 114A are furthest away from the midline 118, an intermediate set of bands 114B are closer to the midline 118, and a distal-most set of bands 114C are closest to the midline 118. In one embodiment, the bands 114 are closer together adjacent the distal end 106 of the tubular wall 102 and farther away from one another when located farther away from the distal end 106 of the tubular wall 102.

Figure 4:
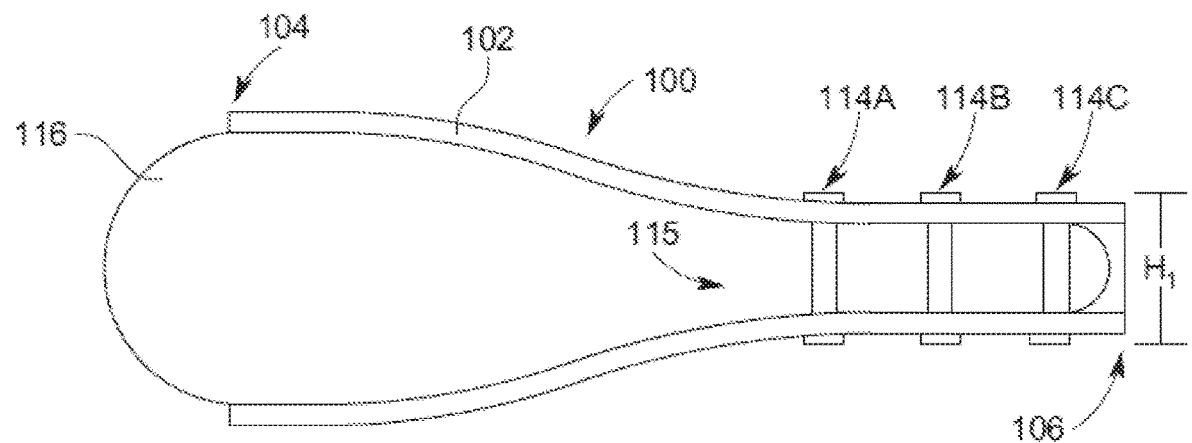
FIG. 4 is a cross-sectional view of the implant delivery sleeve and the implant shown in FIG. 3 taken along line 4-4 of FIG. 3.

Referring to FIGS. 3 and 4, in one embodiment, the bands 114 that comprise the respective proximal bands 114A, intermediate bands 114B, and distal bands 114C have a constant height $H_1$. In one embodiment, an implant 116, such as a breast implant filled with a silicone gel, may be inserted into the proximal opening at the proximal end 104 of the tube-shaped wall 102. As the implant 116 is advanced through the implant delivery channel 115 toward the distal end 106 of the tube-shaped wall 102, the implant deforms and/or changes shape for passing through the constricted area of the implant delivery channel 115 that is bounded by the bands 114A-114C. As shown in FIG. 4, a distal section of the implant 114 is squeezed into a narrower and/or smaller cross-section than a proximal section of the implant for passing through the constricted area created by the series of bands 114A-114C.

Figure 5:
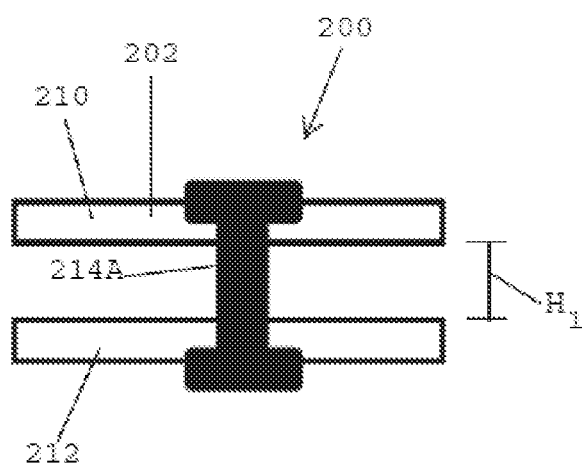
FIG. 5 is a cross-sectional view of a band that interconnects opposing portions of a tubular wall of an implant delivery sleeve, in accordance with one embodiment of the present patent application.

In one embodiment, the respective heights of the bands may change between the proximal end and the distal end of a tube-shaped wall of an implant delivery sleeve. In one embodiment, the bands farther away from the distal end of the tubular wall 102 may have a greater height and the height of the respective bands may decrease as the bands are located closer to the distal end of the tubular wall. For example, FIG. 5 shows a cross-sectional view of a band 214A (e.g., a rivet) that is utilized to interconnect opposing portions 210, 212 of a tube-shaped wall 202 of an implant delivery sleeve 200. The band 214A may be a proximal-most band that has a height $H_1$ that forms a gap $G_1$ between the opposing wall sections 210, 212.

Figure 6:
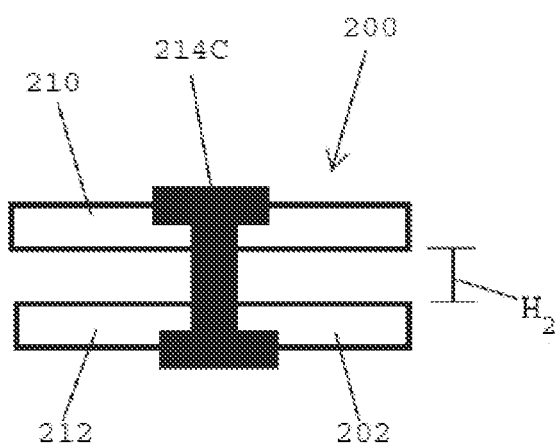
FIG. 6 is a cross-sectional view of a band that interconnects opposing portions of a tubular wall of an implant delivery sleeve, in accordance with one embodiment of the present patent application.

Referring to FIG. 6, in one embodiment, the tube-shaped wall 202 of the implant delivery sleeve 200 shown in FIG. 5 may include a distal band 214C that interconnects the opposing portions 210, 212 of the tube-shaped wall 202. The distal band 214C has a height $H_2$ that is less than the height $H_1$ of the proximal band 214A (FIG. 5) to define a second gap $G_2$ between the opposing wall portions 210, 212 that is less than the first gap $G_1$ created by the proximal band 214A (FIG. 5). As a result of the changing heights of the bands, a tube-shaped wall 202 of the implant delivery sleeve 200 may have bands that define a smaller height adjacent the distal end of the tube-shaped wall and a greater height farther away from the distal end of the tube-shaped wall 202. The progressively smaller heights of the bands constricts the implant delivery channel as an implant moves closer to the distal end of the tube-shaped wall.

Figure 7:
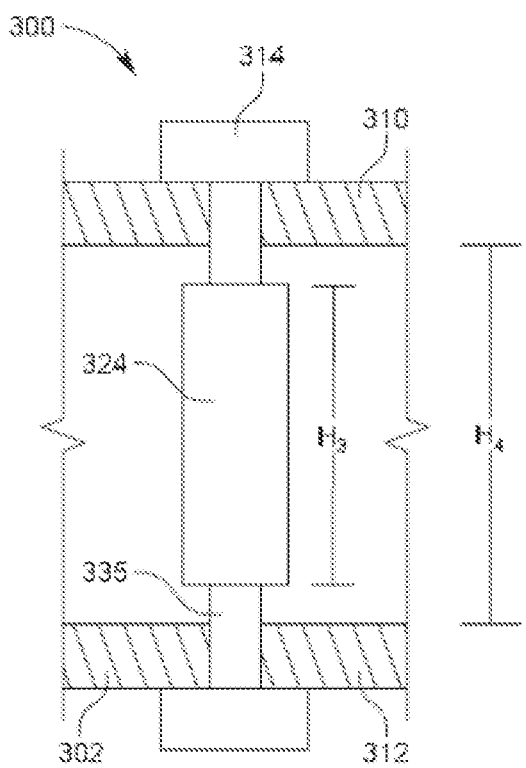
FIG. 7 is a cross-sectional view of a section of an implant delivery sleeve including a band that interconnects opposing portions of a tubular wall of the implant delivery sleeve, the band having a rotatable mid-section for facilitating movement of an implant through an implant delivery channel of the implant delivery sleeve, in accordance with one embodiment of the present patent application.

Referring to FIG. 7, in one embodiment, a band 314 that interconnects opposing wall sections 310, 312 of a tube-shaped wall 302 of an implant delivery sleeve 300 may include a mid-section that rolls to facilitate passage of an implant through the implant delivery channel of the implant delivery sleeve. In one embodiment, the band 314 preferably includes a roller 324 that is adapted to rotate about a shaft 335 of the band 314 to facilitate passage of an implant through the implant delivery sleeve 300. In FIG. 7, the roller 324 has a height $H_3$ that is less than the height $H_4$ between the opposing faces of the first and second wall sections 310, 312 of the tube-shaped wall 302 of the sleeve 300. As such, gaps may be present between the respective upper and lower ends of the roller 324 and the opposing faces of the first and second wall sections 310, 312 of the tube-shaped wall 302.

Figure 8:
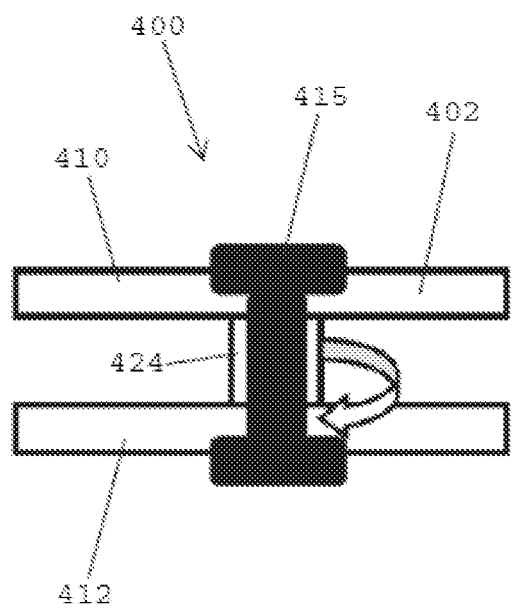
FIG. 8 is a cross-sectional view of a section of an implant delivery sleeve including a band that interconnects opposing portions of a tubular wall of the implant delivery sleeve, the band having a rotatable mid-section for facilitating movement of an implant through an implant delivery channel of the implant delivery sleeve, in accordance with one embodiment of the present patent application.

Referring to FIG. 8, in one embodiment, an implant delivery sleeve 400 preferably includes a band 415 having mid-section that is configured to roll for facilitating the passage of an implant through an implant delivery channel of the implant delivery sleeve. In one embodiment, the bands 415 desirably includes a roller 424 that has a height that matches the distance between the opposing faces of the first and second wall sections 410, 412 of the tube-shaped wall 402 of the implant delivery sleeve 400. As such, there is no gap present between the respective upper and lower ends of the roller 424 and the opposing faces of the first and second wall sections 410, 412 of the tube-shaped wall 402. In other embodiments, the heights of rollers may vary between those that provide the gaps shown in FIG. 7 and those that provide no gaps as shown in FIG. 8.

Figure 9A:
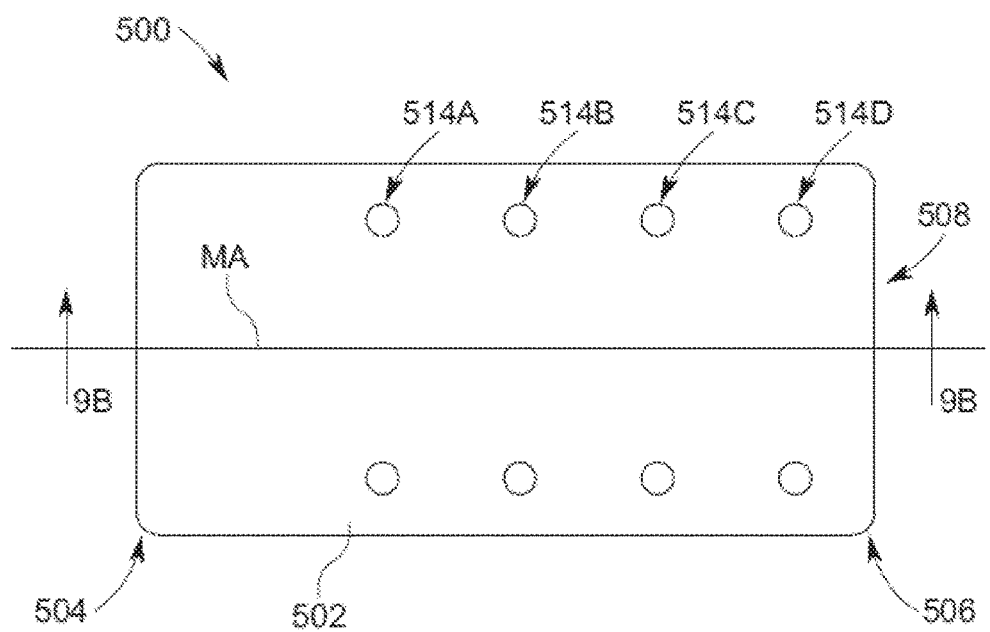
FIG. 9A is a top view an implant delivery sleeve including a tubular wall and bands interconnecting opposing portions of the tubular wall to form a constricted implant delivery channel, in accordance with one embodiment of the present patent application.
Figure 9B:
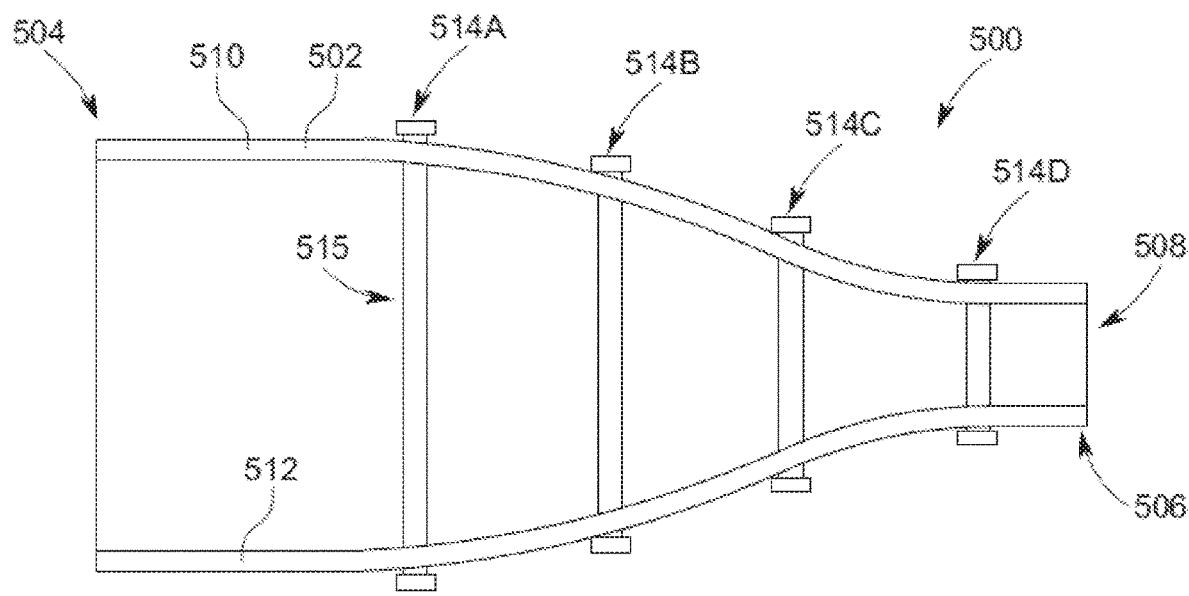
FIG. 9B is a cross-sectional view of the implant delivery sleeve shown in FIG. 9A including the bands interconnecting opposing portions of the tubular wall to form a constricted implant delivery channel.

In one embodiment, the bands may all be installed at the same distance from a middle axis of a tube-shaped wall of an implant delivery sleeve, however, the respective heights of the bands may decrease as the bands are located closer to the distal end of the tube-shaped wall of the implant delivery sleeve. For example, referring to FIGS. 9A and 9B, in one embodiment, an implant delivery sleeve 500 includes a non-tapered, tube-shaped wall 502 having a proximal end 504 and a distal end 506. The implant delivery sleeve 500 preferably includes a series or sets of bands 514A-514D (e.g., rivets) that interconnect opposing wall sections 510, 512 of the tube-shaped wall 502 of the implant delivery sleeve 500. As shown in FIG. 9A, the bands of the different sets of bands 514A-514D are installed at the same distance from the middle axis MA of the tube-shaped wall 502. Referring to FIG. 9B, however, the respective heights of the different sets of bands 514A-514D progressively decrease closer to the distal end 506 of the tube-shaped wall 502 of the implant delivery sleeve 500. In particular, a proximal-most set of bands 514A have a greater height than a first intermediate set of bands 514B, which, in turn, have a greater height than a second intermediate set of bands 514C, which, in turn, have a greater height than a distal-most set of bands 514D. As a result, the size of the implant delivery channel 515 is progressively constricted between the proximal-most set of bands 514A and the distal-most set of bands 514D. An implant passing distally through the implant delivery channel 515 will be squeezed and constricted as it is extruded from the distal opening 508 at the distal end 506 of the tube-shaped wall 502.

Figure 10A:
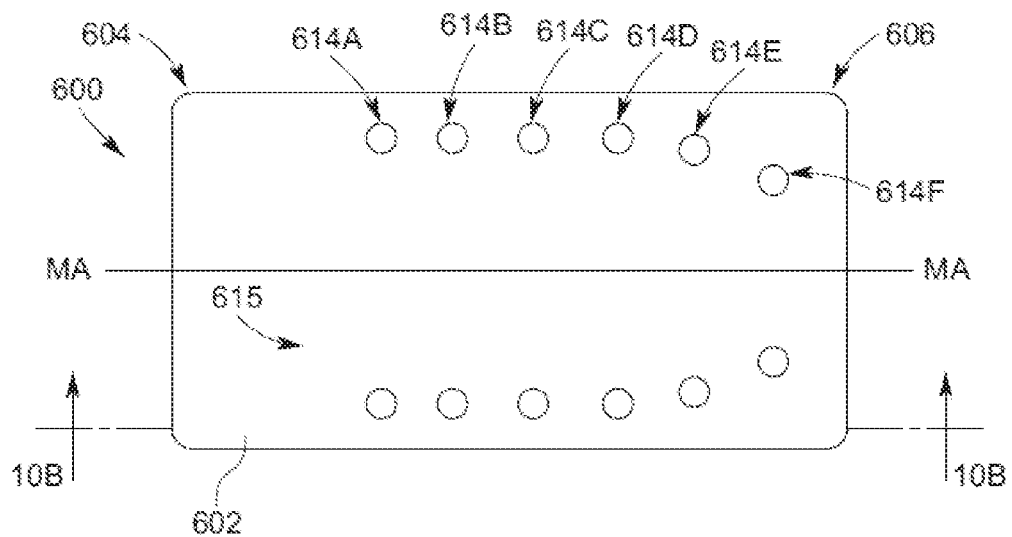
FIG. 10A is a top view an implant delivery sleeve including a tubular wall and bands interconnecting opposing portions of the tubular wall to form a constriction within an implant delivery channel, in accordance with one embodiment of the present patent application.

Referring to FIG. 10A, in one embodiment, an implant delivery sleeve 500 preferably includes sets of bands 614 that interconnect opposing wall sections of a tube-shaped wall 602 of the implant delivery sleeve. The tube-shaped wall 602 has a proximal end 604 and a distal end 606 that defines an implant delivery channel 615 that extends along the length of the tube-shaped wall 602. The bands 614 preferably interconnect opposing wall sections of the tube-shaped wall 602. The tube-shaped wall 602 desirably has a middle axis MA that extends along the length of the tube-shaped wall 602. The bands 614 adjacent the distal end 606 of the tube-shaped wall 602 are generally closer to the middle axis MA than are the bands farther away from the distal end 606 of the tube-shaped wall 602.

Figure 10B:
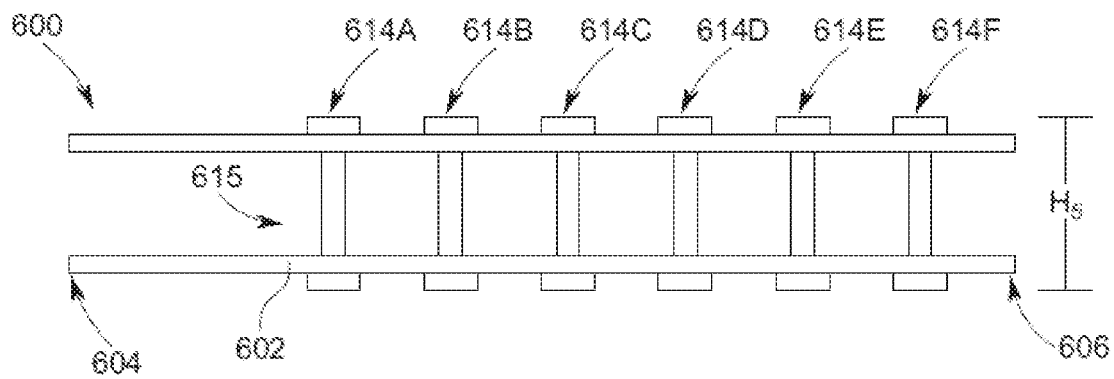
FIG. 10B is a cross-sectional view of the implant delivery sleeve shown in FIG. 10A including the bands interconnecting opposing portions of the tubular wall to form a constriction within the implant delivery channel.

Referring to FIG. 10B, in one embodiment, the sets of bands 614A-614F that interconnect opposing wall sections 610, 612 of the tube-shaped wall 602 desirably have a constant height $H_5$. In one embodiment, the bands 614A-614C that are closer to the proximal end 604 of the tube-shaped wall 602 of the implant delivery sleeve 600 are preferably more elastic and/or stretchable than the bands 614D-614F that are closer to the distal end 606 of the tube-shaped wall 602 of the implant delivery sleeve 600.

In one embodiment, the bands are desirably more elastic farther from the distal end 606 of the tube-shaped wall 602 and less elastic closer to the distal end 606 of the tube-shaped wall 602.

In one embodiment, the first set of bands 614A is more elastic than the second set of bands 614B, which, in turn, is more elastic than the third set of bands 614C. In one embodiment, the third set of bands 614C is more elastic than the fourth set of bands 614D, which, in turn, is more elastic than the fifth set of bands 614E. In one embodiment, the fifth set of bands 614E is more elastic than the sixth set of bands 614F.

Figure 11:
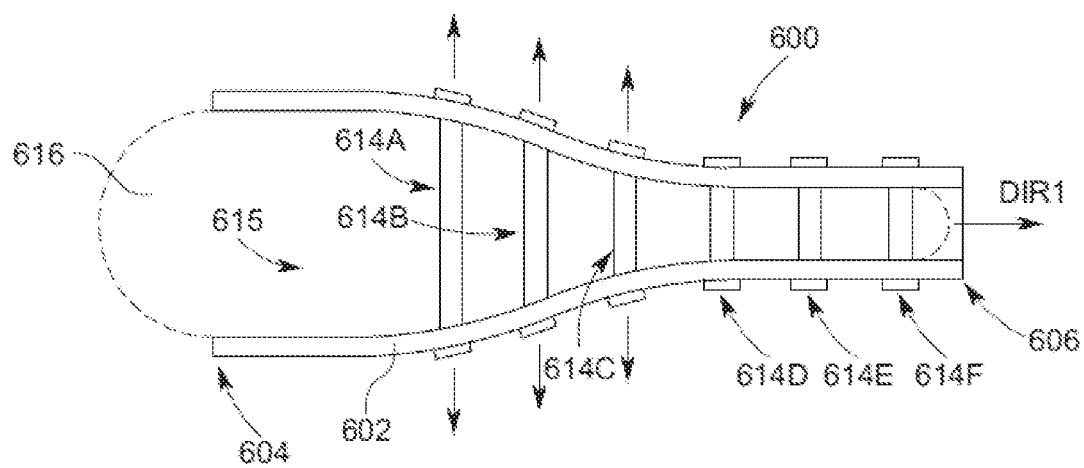
FIG. 11 is a cross-sectional view of the implant delivery sleeve shown in FIGS. 10A and 10B with an implant inserted into a proximal end of the implant delivery sleeve, in accordance with one embodiment of the present patent application.

FIG. 11 shows an implant 616 being inserted into the proximal end 604 of the tube-shaped wall 602 of the implant delivery sleeve 600. As the implant 616 is advanced through the implant delivery sleeve 600 in a distal direction DIR1, the first, second, and third sets of bands 614A-614C stretch for enabling the implant 616 to pass through the implant delivery channel 615 of the implant delivery sleeve 600. The fourth, fifth, and sixth sets of bands 614D-614F are less elastic for squeezing, constricting and/or deforming the shape of the implant 616 as it moves through the implant delivery channel 615 toward the distal end 606 of the tube-shaped wall 602 of the implant delivery sleeve 600.

Figure 12:
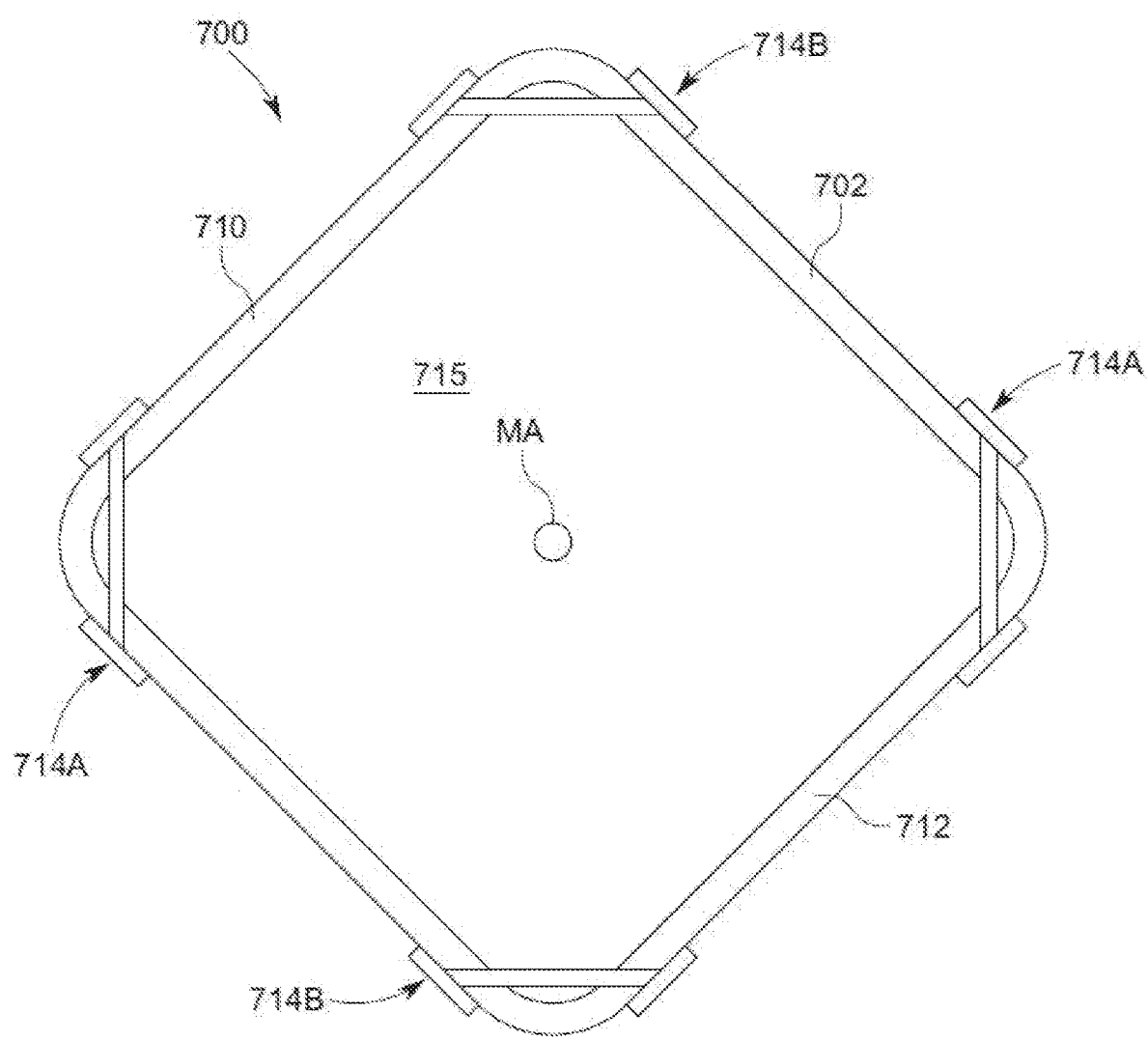
FIG. 12 is a cross-sectional view of an implant delivery sleeve with bands interconnecting portions of a tubular wall to form a constriction within an implant delivery channel, in accordance with one embodiment of the present patent application.

Referring to FIG. 12, in one embodiment, an implant delivery sleeve 700 preferably includes a tube-shaped wall 702 that surrounds an implant delivery channel 715. The tube-shaped wall 702 has a middle axis MA that extends along the length of the tube-shaped wall. In one embodiment, the tube-shaped wall 702 desirable includes a first wall section 710 and an opposing second wall section 712. A first pair of bands 714A mechanically interconnect outer ends of the opposing first and second wall sections 710, 712 for constricting the size of the implant delivery channel 715. A second pair of bands 714B mechanically interconnect central regions of the respective first and second wall sections 710, 712 for farther constricting the size of the implant delivery channel 715. In one embodiment, the bands 714A, 714B are preferably secured adjacent the distal end of the tube-shaped wall 702 of the implant delivery sleeve 700 for constricting the size of the implant delivery channel 715 adjacent the distal end of the tube-shaped wall 702 of the implant delivery sleeve 700.

While the foregoing is directed to embodiments of the present invention, other and farther embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An implant delivery sleeve comprising:
   a tubular wall having a proximal end with a proximal opening, a distal end with a distal opening, and an implant delivery channel extending between the proximal and distal ends of said tubular wall;
   a plurality of bands interconnecting portions of said tubular wall for constricting the implant delivery channel adjacent the distal end of said tubular wall;
   wherein at least one of said bands comprises a rotatable middle section that is configured for engaging said implant to facilitate movement through the implant delivery channel.

2. The implant delivery sleeve as claimed in claim 1, wherein at least some of said bands define a constricted opening that is located at the distal end of said tubular wall, and wherein the constricted opening is smaller than the distal opening at the distal end of said tubular wall.

3. The implant delivery sleeve as claimed in claim 2, wherein the constricted opening is located at a distal end of the implant delivery channel.

4. The implant delivery sleeve as claimed in claim 1, wherein said tubular wall has a cylindrical, non-tapered shape, and wherein the proximal and distal openings of said tubular wall have the same size.

5. The implant delivery sleeve as claimed in claim 1, wherein said tubular wall comprises an elastomeric material.

6. The implant delivery sleeve as claimed in claim 1, wherein at least some of said bands lie in a single plane or in different planes.

7. The implant delivery sleeve as claimed in claim 1, wherein at least some of said bands are configured for engaging an implant passing through the implant delivery channel for deforming said implant within the implant delivery channel.

8. The implant delivery sleeve as claimed in claim 1, wherein said tubular wall has a middle axis that extends from the proximal end to the distal end of said tubular wall.

9. The implant delivery sleeve as claimed in claim 8, wherein said bands have respective heights that decrease as said bands are closer to the distal end and the middle axis of said tubular wall.

10. The implant delivery sleeve as claimed in claim 8, wherein said bands are equidistant from the middle axis and have respective heights that decrease as said bands are closer to the distal end of said tubular wall.

11. The implant delivery sleeve as claimed in claim 8, wherein said bands comprise pairs of bands that are equidistant from the middle axis on opposite sides of the middle axis.

12. The implant delivery sleeve as claimed in claim 1, wherein at least some of said bands are elastic.

13. The implant delivery sleeve as claimed in claim 12, wherein said bands comprise a first group of said bands that are more elastic and a second group of said bands that are less elastic than the first group of said bands.

14. An implant delivery sleeve comprising:
   a tube-shaped outer wall having a proximal end with a proximal opening, a distal end with a distal opening, and an implant delivery channel extending from the proximal opening to the distal opening of said tube-shaped outer wall;
   a plurality of bands disposed inside said tube-shaped outer wall and interconnecting opposing sections of said tube-shaped outer wall for constricting the implant delivery channel adjacent the distal end of said tube-shaped outer wall;
   wherein said tube-shaped outer wall has a middle axis that extends from the proximal end to the distal end of said tube-shaped outer wall, and wherein said bands have respective heights that decrease as said bands are closer to the distal end of said tube-shaped outer wall and the middle axis of said tube-shaped outer wall.

15. The implant delivery sleeve as claimed in claim 14, wherein at least some of said bands define a constricted opening that is located at the distal end of said tube-shaped outer wall.

16. The implant delivery sleeve as claimed in claim 14, wherein said bands are located closer to the distal end of said tube-shaped outer wall than the proximal end of said tube-shaped outer wall.

17. A method of using an implant delivery sleeve comprising:
   obtaining a sleeve including a tubular wall having a proximal end with a proximal opening, a distal end with a distal opening, and an implant delivery channel extending between the proximal and distal openings of said tubular wall, said flexible sleeve including a plurality of bands interconnecting portions of said tubular wall for constricting the size of the implant delivery channel adjacent the distal end of said tubular wall;
   inserting an implant into the proximal opening of said tubular wall so that a distal end of said implant is disposed within the implant delivery channel;
   engaging an outer surface of said tubular wall for closing the first opening at the proximal end of said tubular wall to encapsulate said implant within said tubular wall of said implant delivery sleeve;
   squeezing said tubular wall for applying manual pressure to said implant to push said implant toward the distal end of the implant delivery channel for extruding said implant from the distal opening at the distal end of said tubular wall of said implant delivery sleeve;
   wherein said tubular wall has a middle axis that extends from the proximal end to the distal end of said tubular wall and;
   wherein said bands have respective heights that decrease as said bands are closer to the distal end and the middle axis of said tubular wall.

18. The method as claimed in claim 17, farther comprising:
   forming an incision in a patient;
   inserting the distal end of said tubular wall into the incision;
   during the extruding said implant, passing said implant through the incision and into a tissue pocket.

\* \* \* \* \*